United States Patent [19]

Lamberti

[11] 3,943,165

[45] Mar. 9, 1976

[54] ESTERS OF CARBOXYMETHYLOXYSUCCINIC ACID AND DERIVATIVES THEREOF

[75] Inventor: Vincent Lamberti, Upper Saddle River, N.J.

[73] Assignee: Lever Brothers Company, New York, N.Y.

[22] Filed: July 14, 1972

[21] Appl. No.: 271,852

[52] U.S. Cl.............. 260/484 P; 252/109; 252/170; 252/132; 252/135; 260/78.3 R
[51] Int. Cl.² ......................................... C07C 69/66
[58] Field of Search ...................... 260/484 P, 535 P

[56] References Cited
UNITED STATES PATENTS 3,635,830   1/1972   Lamberti et al. ................ 260/535 P

OTHER PUBLICATIONS

Canadian Journal of Chemistry, Vol. 35, pp. 315–321, 1957.

*Primary Examiner*—Paul J. Killos
*Attorney, Agent, or Firm*—Arnold Grant

[57] ABSTRACT

There are disclosed herein novel ester compounds which can be used as detergent solvents and plasticizers for resins, the compounds having the general formula:

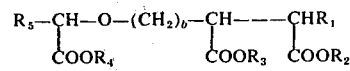

wherein $R_1$ is selected from the group consisting of —H and —$CH_3$; $R_2$, $R_3$ and $R_4$, which may be the same or different substituents, are selected from the group consisting of straight and branched chain alkyl groups having from 1 to 12 carbon atoms, benzyl and cyclohexyl; $R_5$ is selected from the group —H, —$CH_3$ and —$C_2H_5$; and $b=0$ or 1.

8 Claims, No Drawings

ESTERS OF CARBOXYMETHYLOXYSUCCINIC ACID AND DERIVATIVES THEREOF

BACKGROUND OF THE INVENTION

Field of the Invention and Prior Art

This application, relating to esters of carboxymethyloxysuccinic acid, is copending with applications of Lamberti et al. Ser. No. 80,166, filed Oct. 12, 1970 now U.S. Pat. No. 3,692,685, which discloses and claims the salts of carboxymethyloxysuccinic acid and Ser. No. 139,225, filed Apr. 30, 1971, which discloses and claims homologs and analogs of the salts of carboxymethyloxysuccinic acid.

One compound falling within the genus of the present invention has been suggested by the prior art, viz., the triethyl ester of carboxymethyloxysuccinic acid, is disclosed by von Rudloff et al Canadian J. Chem. 35 315 (1957) as an intermediate in a synthesis. However, no uses are disclosed for the compound. The other compounds of the present invention have not been described or suggested in the art.

SUMMARY OF THE INVENTION

The present invention relates to a group of novel ester compounds, the compounds being useful as plasticizers for a broad range of resins, especially polyvinylchloride, and as detergent solvents having utility in removing oil based stains particularly on polyester and polyester blend fabrics. The compounds of the present invention have the general formula:

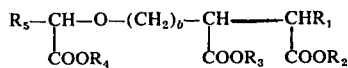

wherein $R_1$ is selected from the group consisting of —H and —$CH_3$; $R_2$, $R_3$ and $R_4$, which may be the same or different substituents, are selected from the group consisting of straight and branched chain alkyl groups having from 1 to 12 carbon atoms, benzyl and cyclohexyl; $R_5$ is selected from the group —H, —$CH_3$ and —$C_2H_5$; and, $b=0$ or 1.

DETAILED DESCRIPTION OF THE INVENTION

The present invention relates to novel compounds which can be broadly classified as esters of carboxymethyloxysuccinic acid, and derivatives thereof, the esters having the general formula

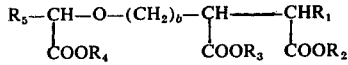

wherein $R_1$ is selected from the group consisting of —H and —$CH_3$; $R_2$, $R_3$ and $R_4$, which may be the same or different substituents, are selected from the group consisting of straight and branched chain alkyl groups having from 1 to 12 carbon atoms, benzyl and cyclohexyl; $R_5$ is selected from the group —H, —$CH_3$, —$C_2H_5$; and, $b=0$ or 1.

PREPARATION OF BASIC STARTING MATERIAL

The sodium and calcium salts of carboxymethyloxysuccinic acid, which will be the basic starting materials for the esterification reactions to be hereafter described, may be prepared as follows:

Maleic anhydride (0.2 mole; 19.6 g) is dissolved in water (100 ml) at room temperature and stirred for 10-15 minutes to convert it to the acid. Glycolic acid (0.24 mole; 18.3 g) is then added and dissolved with stirring. Calcium hydroxide, (ca 0.36 mole; 27 g), sufficient to attain a pH of 11.4 as measured initially at 25°C is next added while stirring the reaction mixture vigorously. The mixture is heated to reflux and maintained at reflux for two hours while stirring vigorously. After cooling to 60°C, finely ground sodium carbonate (0.4 mole; 42.4 g) is added and stirring continued for 15 minutes at 60°C. The mixture is then cooled to room temperature and the suspended $CaCO_3$ filtered off and washed with water. The filtrate (including the washings) contains the product, trisodium carboxymethyloxysuccinate, in yields of about 95% as determined by NMR analysis.

Anhydrous trisodium carboxymethyloxysuccinate may be isolated by evaporation of the filtrate and drying of the residue. Alternatively, the filtrate may be treated with alcohol or acetone to precipitate the desired trisodium carboxymethyloxysuccinate which is then isolated by filtration and further dried to remove any water of hydration if desired. Further purification may be accomplished by recrystallization from 80/20 (V/V) alcohol/water.

In preparing the esters of carboxymethyloxysuccinic acid either trisodium carboxymethyloxysuccinate prepared as above or the calcium salt of carboxymethyloxysuccinic acid may be used. The calcium salt is readily obtained by filtration of the reaction mixture above after the 2 hour reflux period. The dry calcium salt has the empirical formula $C_{12}H_{10}O_{14}Ca_3$.

Since water is removed in the esterification reactions, the starting sodium or calcium salts of carboxymethyloxysuccinic acid may be used in the form of their hydrates.

From these basic starting materials, $C_1$ to $C_4$ alkyl esters of carboxymethyloxysuccinic acid may be prepared as follows:

EXAMPLE 1

A mixture of 103 g (0.4 mole) of trisodium carboxymethyloxysuccinate or 0.2 mole of the calcium salt of carboxymethyloxysuccinic acid, 3.6 moles of the desired alcohol (methanaol, ethanol, etc.), 360 ml of ethylene dichloride and 45 ml of concentrated $H_2SO_4$ is stirred and refluxed for 13 hours. The precipitated sodium (or calcium) sulfate is filtered off and the filtrate washed repeatedly with saturated sodium bicarbonate solution followed by water until the washings are neutral. The ethylene dichloride layer is then dried and evaporated to give a residue of ester which is finally distilled in vacuo. In this way the following esters of carboxymethyloxysuccinic acid are obtained:

|             | b.p. °C/mm      |
|-------------|-----------------|
| trimethyl   | 117/0.25        |
| triethyl    | 123–125/0.30    |
| tri-n-propyl| 134–138/0.10–0.15 |
| tributyl    | 158–160/0.2–0.3 |

Similarly, $C_5$ to $C_{12}$ alkyl esters of carboxymethyloxysuccinic acid may be prepared as follows:

EXAMPLE 2

A mixture of 25.8 g (0.1 mole) of the sodium salt or 0.05 mole of the calcium salt of carboxymethyloxysuccinic acid, 0.9 mole of the desired alcohol (e.g., n-pentyl, n-hexyl 2-ethylhexyl, etc.), 100 ml of ethylene dichloride and 12 ml of concentrated sulfuric acid is stirred and refluxed for 30 hours. The precipitated sodium (or calcium) sulfate is filtered off and the filtrate mixed with 400 ml of ether. The ether/ethylene dichloride layer is then washed repeatedly with saturated sodium bicarbonate solution and water until the washings are neutral. The organic layer is then dried and evaporated to yield the residue which is then partially distilled (oil batch to 140°C) at 0.1 mm to remove unreacted alcohol. In this way the following esters of carboxymethyloxysuccinic acid are obtained in approximately 90% yields and in purities of 85–95% as determined by NMR analysis: tri-n-pentyl, tri-n-hexyl, tri-n-octyl, tri(2-ethylhexyl), tri-n-decyl and tri-n-dodecyl.

Mixed alkyl esters may be prepared by utilizing a mixture of the desired alcohols in the above examples. Alternatively, another method of preparing the higher esters (homogeneous and mixed) is as follows:

EXAMPLE 3

A mixture of 160 g (1.1 mole) of Alfol 810 (a commercial synthetic alcohol containing about 45% 1-octanol and 55% 1-decanol), 85 g (0.33 mole of trisodium carboxymethyloxysuccinate and 100 ml of toluene are placed in a flask), 57 g of concentrated sulfuric acid are slowly added with stirring. The mixture is then heated to reflux and water is continuously removed using a condenser/Dean Stark trap set-up. The toluene layer in the distillate is continuously returned to the reaction flask. When no more water distills over, the reaction mixture is cooled to about 50°C, filtered to remove insoluble salts and then washed repeatedly with saturated sodium bicarbonate solution followed by water until the washings are neutral. The organic layer is then stripped of solvent and other volatiles by heating gradually to 140°C under a vacuum of 0.1mm. The residue, which consists of a random mixture of $C_8$–$C_{10}$ alkyl esters of carboxymethyloxysuccinic acid, is finally decolorized by treatment with 0.1% by weight of activated carbon at 90°C for 1 hour followed by filtration.

Esters according to the general formula of the present invention wherein substituents $R_1$ and $R_5$ are other than —H and wherein $b=1$ can be obtained by modifying the basic starting material described above to provide the appropriate substituents prior to the esterification reactions of Examples 1–3. That is, in the reaction to prepare salts of carboxymethyloxysuccinic acid, glycolic acid can be considered as constituent A, and maleic acid can be considered as constituent B. Thus, if it is desired to prepare a starting material for the esterification reactions of Examples 1–3, wherein substituent $R_1$ is —$CH_3$, constituent B would be changed from maleic acid to methylmaleic acid. Similarly, if it is desired that substituent $R_5$ be —$CH_3$, constituent A would be changed from glycolic acid to lactic acid; and, if it is desired that substituent $R_5$ be —$C_2H_5$, constituent A would be alpha-hydroxybutyric acid. Finally, if an ester according to the above general formula is to be prepared wherein $b=1$, the starting material reaction would utilize itaconic acid as constituent B. When substituent A is either lactic acid or alpha-hydroxybutyric acid, the initial pH of the reaction mixture is adjusted to the 11.8–12.1 range with calcium hydroxide instead of 11.4. In each case, the esterification reaction would then proceed according to Example 1 for $C_1$ to $C_4$ alkyl esters and mixed esters thereof and according to Example 2 and 3 for $C_5$ to $C_{12}$ alkyl esters, benzyl and cyclohexyl esters and mixed esters thereof. A naming system for these compounds is as follows:

| $R_1$ | $R_2$ | $R_3$ | $R_4$ | $R_5$ | b | Ester |
|---|---|---|---|---|---|---|
| H | $CH_3$ | $CH_3$ | $CH_3$ | H | 0 | trimethyl carboxymethyloxysuccinate |
| $CH_3$ | $CH_3CH_2$ | $CH_3CH_2$ | $CH_3CH_2$ | H | 0 | triethyl α-carboxymethyloxy-β-methyl succinate |
| H | n-$C_3H_7$ | n-$C_3H_7$ | n-$C_3H_7$ | $CH_3$ | 0 | tripropyl lactoxysuccinate |
| H | n-$C_4H_9$ | n-$C_4H_9$ | n-$C_4H_9$ | $C_2H_5$ | 0 | tributyl [1-(carboxy)propyloxy]succinate |
| H | n-$C_5H_{11}$ | n-$C_5H_{11}$ | n-$C_5H_{11}$ | H | 1 | tripentyl carboxymethyloxymethylsuccinate |
| H | ←—— mixed n-$C_6H_{13}$/n-$C_8H_{17}$ ——→ | | | $CH_3$ | 0 | tri(random hexyl/octyl) lactoxysuccinate |

These compounds find particular utility as plasticizers for resins and as detergent solvents in detergent compositions especially for oil and grease type stains in polyester and polyester blend fabrics.

As plasticizers, they can be used with a variety of plastics such as polyvinyl chloride, polyvinyl chloride copolymers, polyamides such as nylon-6 and nylon 6,6, polyethylene, polypropylene, polystyrene, polyesters such as polyethylene terephthalate, polyurethanes, polycarbonates, polyacrylates, polyacrylonitrile, polymethacrylate, phenolic resins, epoxyresins, cellulose nitrate cellulose acetate and ethyl cellulose, etc. All of the esters within the present invention are particularly advantageous when compared to the plasticizers most normally used in the art such as dioctyl phthalate, di-2-ethylhexyl phthalate and di-2-ethylhexyl adipate for a number of reasons, most notably their relatively lower volatility and the fact that the parent compound, e.g., carboxymethyloxysuccinic acid, from which the esters are derived is non-toxic, non-teratogenic and completely biodegradable under both aerobic and anaerobic conditions. The latter features are especially important since plasticizers eventually find their way into the environment (or into contact with humans or their food) and gradually release, to the environment, the parent compound and the starting alcohol by chemical or bacterial action.

Preferred embodiments of the present invention for use as plasticizers for plastics are the esters derived from $C_4$ to $C_{12}$ alcohols, most notably the esters of 1) carboxymethyloxysuccinic acid, 2) lactoxysuccinic acid, 3) carboxymethyloxymethylsuccinic acid, and 4) α-carboxymethyloxy-β-methylsuccinic acid: tributyl-, tri(isobutyl)-, tripentyl-, trihexyl-, tricyclohexyl-, triheptyl-, trioctyl-, tri(2-ethylhexyl)-, tri(isoctyl)-, tri (mixed hexyl/octyl-), trinonyl-, tridecyl-, tri(isodecyl)-, tri(mixed n-octyl/n-decyl-), triundecyl-, tridodecyl-, and tribenzyl.

Use levels for the esters of the present invention as plasticizers are on the order from about 1 to about 75 weight percent, based on the weight of the total composition, with a preferred range of from about 15 to about 65 weight percent. The following example demonstrates the facility of these esters as plasticizers for plastics.

EXAMPLE 4

Tri(2-ethylhexyl) carboxymethyloxysuccinate was incorporated as a plasticizer in the preparation of polyvinyl chloride film as follows

FORMULATION

|  | Parts by Weight |
|---|---|
| S-PVC resin (K value, 68–72) | 100 |
| plasticizer | 65 |
| BaCd stabilizer | 2 |
| wax lubricant | 0.5 |

Using a mixing roller at 170° (7 min.) followed by post-pressing the film at 170°C under contact pressure for 2 minutes, a good plasticized film (1.3 mm) of polyvinyl chloride was obtained. Cold resistance was −39°C compared to −36°C for a control PVC film made using di-2-ethylhexyl phthalate (DOP) as the plasticizer.

These esters also have considerable utility as detergent solvents in detergent compositions particularly for oil and grease type stains on polyester and polyester blend fabrics. In detergent compositions the invention will generally include a synthetic builder and a water soluble organic detergent compound. Detergent compounds useful in the present invention are the anionic (soap and non-soap), nonionic, zwitterionic and ampholytic compounds. The general nature of these detergent compounds is not an essential feature of the present invention. Moreover, such detergent compounds are well-known to those skilled in the detergent art. Typical of such detergents are those described in the well-known books entitled "Surface Active Agents" by Schwartz and Perry and "Surface Active Agents and Detergents" by Schwartz, Perry and Berch, both by Interscience Publishers, New York, New York, the disclosures of which are incorporated by reference herein.

The present invention can also be used with a wide variety of builder compounds such as sodium tripolyphosphate, sodium carbonate, sodium silicate, the alkali metal, ammonium and substituted ammonium salts of oxydisuccinic acid, oxydiacetic acid, carboxymethyloxymalonic acid, carboxymethloxysuccinic acid, lactoxysuccinic acid, citric acid, mellitic acid, tetrahydrofurantetracarboxylic acid, polyacrylic acid, nitrilotriacetic acid, oxidized starches and mixtures thereof.

As detergent solvents the preferred esters are those derived from straight or branched chain 2–6 carbon alcohols, although each of the compounds within the present invention functions effectively in this capacity. Use levels are on the order of from about 1 to about 35 weight percent based on the weight of the total composition, with a preferred range of from about 2 to about 20 weight percent and a most preferred range of from about 2 to about 10 weight percent. The following test results demonstrates this utility:

EXAMPLE 5

Four Dacron/cotton (65–35%) Khaki permanent press (Pants weight) test pieces (4½ × 6 inches) are first soiled by adding 3 drops of dirty crankcase oil on the center of the cloth and the stain allowed to set for 1 hour. The test cloths are then washed in the Terg-O-Tometer at 120°F, 180 ppm (2:1 $Ca^{++}/Mg^{++}$) hardness, 90 cycles per minute agitation, with a 5% solution of the detergent product described below (i.e., 50 g/liter) for 15 minutes and then hand squeezed to remove excess water. Finally the cloths are given a 20 minute wash at the standard use level (e.g. 0.144%) under the same conditions followed by a 1 minute rinse. After drying the washed cloths, the degree of stain removal is rated visually according to the scale below:

VISUAL GRADING SYSTEM

0 = Complete removal
1 = Very slight remaining stain
2 = Slight remaining stain
3 = Moderate stain removal
4 = Poor stain removal
5 = Very poor stain removal
6 = Equal to original stain (The above laboratory procedure has been found to correlate with the regular procedure used by housewives whereby a paste of the product is applied to the spot prior to washing the fabric in the washing machine.)

The detergent product used is formulated as follows:

| COMPONENT | % ACTIVE |
|---|---|
| Tergitol 15-S-9 (adduct of nine moles of ethylene oxide per mole of random secondary alcohol derived from $C_{11}$–$C_{15}$ paraffins) | 15.0 |
| Sodium Tripolyphosphate | 40.0 |
| Sodium Carboxymethylcellulose | 0.3 |
| RU Silicate Solids ($SiO_2$:$Na_2O$ ratio of 2.4:1) | 4.2 |
| Miscellaneous (mainly fluorescent dyes, colorants, perfume) | 0.6 |
| "Detergent Solvent" | 4.0 |
| Silica absorbent for detergent solvent | 3.0 |
| Water | 12.0 |
| Sodium sulfate | balance |

Ten such formulations utilizing the following "Detergent Solvents" were prepared and evaluated as described above:

A — dibutyl phthalate (control)
B — trimethyl carboxymethyloxysuccinate
C — triethyl carboxymethyloxysuccinate
D — tripropyl carboxymethyloxysuccinate
E — tributyl carboxymethyloxysuccinate
F — trihexyl carboxymethyloxysuccinate
G — tri-(2-ethylhexyl) carboxymethyloxysuccinate
H — trioctyl carboxymethyloxysuccinate
I — tridecyl carboxymethyloxysuccinate
J — tridodecyl carboxymethyloxysuccinate The results obtained using the visual grading system were as follows:

| Sample Code | Visual Grading Code |
|---|---|
| A | 2 |
| B | 2 |
| C | 1 |
| D | 1 |
| E | 2 |
| F | 1 |
| G | 2 |
| H | 2 |
| I | 2 |

-continued

| Sample Code | Visual Grading Code |
|---|---|
| J | 2 |

The table clearly shows that the esters according to the present invention are equal to and in some instances superior to dibutyl phthalate which is considered to be the standard for detergent compositions of this type.

EXAMPLE 6

Other suitable formulations with the "Detergent Solvent" being the same as above are as follows:

| COMPONENT | % ACTIVE |
|---|---|
| LAS (sodium linear secondary alkyl ($C_{10}$–$C_{15}$) benzene sulfonate) | 18 |
| Sodium Tripolyphosphate | 35 |
| Sodium Carboxymethylcellulose | 0.3 |
| RU Silicate Solids | 4.2 |
| Miscellaneous (mainly fluorescent dyes, colorants, perfume) | 0.6 |
| "Detergent Solvent" | 15.0 |
| Silica absorbent for detergent solvent | 6.0 |
| Water | 12.0 |
| Sodium sulfate | balance |

EXAMPLE 7

| COMPONENT | % ACTIVE |
|---|---|
| LAS | 28.0 |
| Trisodium Citrate | 35.0 |
| Sodium carboxymethylcellulose | 0.3 |
| RU Silicate Solids | 8.0 |
| Miscellaneous (mainly fluorescent dyes, colorants, perfume) | 0.6 |
| "Detergent Solvent" | 10.0 |
| Silica absorbent for detergent solvent | 5.0 |
| Water | 10.0 |
| Sodium sulfate | balance |

EXAMPLE 8

| COMPONENT | % ACTIVE |
|---|---|
| LAS | 25.0 |
| Trisodium carboxymethyloxysuccinate | 30.0 |
| Sodium carboxymethylcellulose | 0.3 |
| RU Silicate Solids | 4.0 |
| Miscellaneous (mainly fluorescent dyes, colorants, perfume) | 0.6 |
| "Detergent Solvent" | 7.0 |
| Silica absorbent for detergent solvent | 4.0 |
| Water | 10.0 |
| Sodium sulfate | balance |

EXAMPLE 9

| COMPONENT | % ACTIVE |
|---|---|
| LAS | 25.0 |
| Trisodium carbpxymethyloxysuccinate | 30.0 |
| Sodium carboxymethylcellulose | 0.3 |
| RU Silicate Solids | 4.2 |
| Miscellaneous (mainly fluorescent dyes, colorants, perfume) | 0.6 |
| "Detergent Solvent" | 2.0 |
| Water | 10.0 |
| Sodium sulfate | balance |

EXAMPLE 10

| COMPONENT | % ACTIVE |
|---|---|
| Tergitol 15-S-9 | 30.0 |
| Triethanolamine Neodol 25-3EO sulfate (the triethanol amine salt of the sulfated adduct of 3 moles of ethylene oxide per mole of Neodol 25 which is a mixture of linear primary alcohols containing 12–15 carbon atoms) | 10.0 |
| Coconut monoethanolamide | 2.0 |
| "Detergent Solvent" | 6.0 |
| Ethanol | 9.0 |
| Sodium carboxymethylcellulose | 0.3 |
| Miscellaneous (mainly fluorescent dyes, colorants and perfume) | 0.6 |
| Water | balance |

Here, again, the lower volatility of the esters of carboxymethyloxysuccinic acid relative to dibutyl phthalate is especially advantageous since little or no loss of the ester occurs during processing of the detergent powder. A still further advantage is that should any of the ester hydrolyze during detergent processing or during the washing process, the resultant salt is an excellent detergent builder, whereas in the case of the phthalate salt no useful detergent properties are obtained. The non-toxic and biodegradable properties of the parent acid from which the esters are derived are especially important since detergent wastes are generally discharged directly into the water environment.

The esters can also be utilized in regular spot cleaners or pre-wash spot cleaners of the spray or aerosol type. Thus, a 5 to 10% solution of the desired ester in a 50/50 mixture of Freon 11/Freon 12 or Freon 12/Freon 13 propellants is admirably suitable for dispensing from an aerosol container for spot cleaning of fabrics, especially polyester, polyester blends and other synthetics and also as a pre-wash spot cleaner for such fabrics prior to washing the fabric in a washing machine with a conventional laundry detergent formulation. (phosphate or non-phosphate based).

It will be appreciated that various changes and modifications, in addition to those set forth above, may be made by those skilled in the art without departing from the essence of the present invention and that accordingly the invention is to be limited only within the scope of the appended claims.

What is claimed is:

1. A compound having the formula

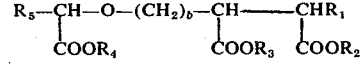

wherein $R_1$ is selected from the group consisting of —H and —$CH_3$; $R_2$, $R_3$ and $R_4$, which may be the same or different substituents, are selected from the group consisting of straight and branched chain alkyl groups having from 1 to 12 carbon atoms, benzyl and cyclohexyl; $R_5$ is selected from the group consisting of —H, —$CH_3$ and —$C_2H_5$; and, $b$=0,1.

2. A compound as defined in claim 1 wherein $R_1$ is —H.

3. A compound as defined in claim 1 wherein $R_1$ is —$CH_3$.

4. A compound as defined in claim 1 wherein $R_2$, $R_3$ and $R_4$ are selected from the group consisting of straight and branched chain alkyl groups having from 1 to 12 carbon atoms.

5. A compound as defined in claim 1 wherein $R_2$, $R_3$ and $R_4$ are selected from the group consisting of straight and branched chain alkyl groups having from 1 to 12 carbon atoms and benzyl.

6. A compound as defined in claim 1 wherein $R_2$, $R_3$ and $R_4$ are selected from the group consisting of straight and branched chain alkyl groups having from 1 to 12 carbon atoms and cyclohexyl.

7. A compound as defined in claim 1 wherein $R_5$ is selected from the group consisting of —H and —$CH_3$.

8. A compound as defined in claim 1 wherein $R_5$ is selected from the group consisting of —$CH_3$ and $C_2H_5$.

* * * * *